US008318905B2

(12) United States Patent
Kroczek (10) Patent No.: US 8,318,905 B2
(45) Date of Patent: Nov. 27, 2012

(54) ANTIBODIES FOR DEPLETION OF ICOS-POSITIVE CELLS IN VIVO

(76) Inventor: Richard Kroczek, Berlin (DE)

( * ) Notice: Subject to any disclaimer, the term of this patent is extended or adjusted under 35 U.S.C. 154(b) by 1381 days.

(21) Appl. No.: 11/578,215

(22) PCT Filed: Apr. 22, 2005

(86) PCT No.: PCT/EP2005/004349
§ 371 (c)(1),
(2), (4) Date: Nov. 28, 2007

(87) PCT Pub. No.: WO2005/103086
PCT Pub. Date: Nov. 3, 2005

(65) Prior Publication Data
US 2012/0039902 A1  Feb. 16, 2012

Related U.S. Application Data

(60) Provisional application No. 60/581,479, filed on Jun. 21, 2004.

(30) Foreign Application Priority Data

Apr. 23, 2004  (EP) ..................................... 04009659

(51) Int. Cl.
*C07K 16/00* (2006.01)
*A61K 39/395* (2006.01)
(52) U.S. Cl. .................................. 530/387.1; 424/130.1
(58) Field of Classification Search .......................... None
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 4,946,778 A | 8/1990 | Ladner et al. | |
| 5,219,996 A | 6/1993 | Bodmer et al. | |
| 5,223,409 A | 6/1993 | Ladner et al. | |
| 5,403,484 A | 4/1995 | Ladner et al. | |
| 5,427,908 A | 6/1995 | Dower et al. | |
| 5,516,637 A | 5/1996 | Huang et al. | |
| 5,571,698 A | 11/1996 | Ladner et al. | |
| 5,580,717 A | 12/1996 | Dower et al. | |
| 5,585,089 A | 12/1996 | Queen et al. | |
| 5,658,727 A | 8/1997 | Barbas et al. | |
| 5,677,425 A | 10/1997 | Bodmer et al. | |
| 5,698,426 A | 12/1997 | Huse | |
| 5,733,743 A | 3/1998 | Johnson et al. | |
| 5,750,753 A | 5/1998 | Kimae et al. | |
| 5,780,225 A | 7/1998 | Wigler et al. | |
| 5,821,047 A | 10/1998 | Garrard et al. | |
| 5,969,108 A | 10/1999 | McCafferty et al. | |
| 6,645,494 B1 * | 11/2003 | Boer De et al. | 424/183.1 |
| 7,030,225 B1 * | 4/2006 | Tamatani et al. | 530/387.1 |
| 7,125,551 B2 | 10/2006 | Kroczek | |
| 7,132,099 B2 | 11/2006 | Kroczek | |
| 7,259,247 B1 | 8/2007 | Kroczek | |
| 2002/0102658 A1 * | 8/2002 | Tsuji et al. | 435/70.21 |
| 2002/0115831 A1 | 8/2002 | Tamatani et al. | |
| 2002/0151685 A1 | 10/2002 | Tamatani et al. | |
| 2002/0156242 A1 | 10/2002 | Tamatani et al. | |
| 2002/0164697 A1 | 11/2002 | Coyle et al. | |
| 2004/0120945 A1 | 6/2004 | Tamatani et al. | |
| 2004/0151720 A1 | 8/2004 | Tamatani et al. | |

FOREIGN PATENT DOCUMENTS

| | | |
|---|---|---|
| EP | 0368684 B1 | 3/1994 |
| EP | 0392745 B1 | 11/1994 |
| EP | 0916336 A1 | 5/1999 |
| EP | 1158004 A2 | 11/2001 |
| EP | 0948544 B1 | 5/2003 |
| EP | 1374902 A1 | 1/2004 |
| EP | 0984023 | 4/2007 |
| WO | WO 86/01533 | 3/1986 |
| WO | WO 88/01649 | 3/1988 |
| WO | WO 89/10398 | 11/1989 |
| WO | WO 90/02809 | 3/1990 |
| WO | WO 90/04180 | 4/1990 |
| WO | WO 91/10737 | 7/1991 |
| WO | WO 92/01047 | 1/1992 |
| WO | WO 92/02551 | 2/1992 |
| WO | WO 92/18619 | 10/1992 |
| WO | WO 92/22853 | 12/1992 |
| WO | WO 93/06213 | 4/1993 |
| WO | WO 93/08829 | 5/1993 |
| WO | WO 93/11236 | 6/1993 |
| WO | WO 95/15982 | 6/1995 |

(Continued)

OTHER PUBLICATIONS

Alters et al., "Mechanisms of Anti-CD4 Mediated Depletion and Immunotherapy: A Study Using a Set of Chimeric Anti-CD4 Antibodies," *J Immunol.* 144(12): 4587-4592 (1990).

(Continued)

*Primary Examiner* — Ilia Ouspenski
(74) *Attorney, Agent, or Firm* — Clark & Elbing LLP (57) ABSTRACT

The present invention relates generally to binding agents useful in the selective depletion of T cells in vivo. More specifically, the invention relates to ICOS-binding agents which once bound to ICOS expressed on the surface of cells, in particular ICOS-bearing activated T cells, result in the in vivo depletion of cells to which they are bound. Methods of treating T cell related diseases using said ICOS-binding agents, and pharmaceutical compositions comprising said ICOS-binding agents, a method of identifying an ICOS-binding agent, and monoclonal anti-ICOS antibodies capable of eliminating cells in vivo which express ICOS on their surface are also provided.

14 Claims, 5 Drawing Sheets

FOREIGN PATENT DOCUMENTS

| | | |
|---|---|---|
| WO | WO 95/20401 | 8/1995 |
| WO | WO 97/11689 | 4/1997 |
| WO | WO 97/35564 | 10/1997 |
| WO | WO 98/23291 | 6/1998 |
| WO | WO 98/24884 | 6/1998 |
| WO | WO 98/38216 | 9/1998 |
| WO | WO 99/15553 | 4/1999 |
| WO | WO 00/46240 | 8/2000 |

OTHER PUBLICATIONS

Ames et al., "Conversion of Murine Fabs Isolated From a Combinatorial Phage Display Library to Full Length Immunoglobulins," *Journal of Immunological Methods* 184:177-186 (1995).

Aslam et al., "Bioconjugation: Protein Coupling Techniques for the Biomedical Sciences," Macmillian Reference Ltd. pp. 548-553 (1998).

Babcook et al., "A Novel Strategy for Generating Monoclonal Antibodies from Single, Isolated Lymphocytes Producing Antibodies of Defined Specificities," *Proc Natl Acad Sci U S A* 93:7843-7848 (1996).

Beste et al., "Small Antibody-Like Proteins with Prescribed Ligand Specificities Derived from the Lipocalin Fold," *Proc Nat Acad Sci U S A* 96:1898-1903 (1999).

Bonhagen et al., "ICOS+ Th Cells Produce Distinct Cytokines in Different Mucosal Immune Responses," *Eur J Immunol.* 33:392-401 (2003).

Brinkmann et al., "Phage Display of Disulfide-Stabilized Fv Fragments," *J Immunol Methods* 182:41-50 (1995).

Brock et al., "Induction Therapy in Lung Transplantation: A Prospective, Controlled Clinical Trial Comparing OKT3, Anti-Thymocyte Globulin, and Daclizumab," *J Heart Lung Transplant.* 20: 1282-1290 (2001).

Bruggemann, "Chapter 11: Construction, Expression, and Function of Chimeric Antibodies," The Human IgG Subclasses: Molecular Analysis of Structure, Function, and Regulation. Pergamon Press: pp. 195-215 (1990).

Buonfiglio et al., "Characterization of a Novel Human Surface Molecule Selectively Expressed by Mature Thymocytes, Activated T Cells and Subsets of T Cell Lymphomas," *Eur J Immunol.* 29:2863-2874 (1999).

Burton et al., "Human Antibodies from Combinatorial Libraries," *Adv Immunol.* 57:191-280 (1994).

Carreno et al., "The B7 Family of Ligands and Its Receptors: New Pathways for Costimulation and Inhibition of Immune Responses," *Annu Rev Immunol.* 20:29-53 (2002).

Chapman, "PEGylated Antibodies and Antibody Fragments for Improved Therapy: A Review," *Adv Drug Deliv Rev.* 54:531-545 (2002).

Cole et al., "The EBV-Hybridoma Technique and its Application to Human Lung Cancer," *Monoclonal Antibodies—and Cancer Therapy* 77-96 (1985).

Croft et al., "Co-Stimulatory Members of the TNFR Family: Keys to Effective T-Cell Immunity?" *Nat Rev Immunol.* 3:609-620 (2003).

Dubowchik et al, "Receptor-Mediated and Enzyme-Dependent Targeting of Cytotoxic Anticancer Drugs," *Pharmacology & Therapeutics.* 83:67-123 (1999).

Felix, "Chapter 16: Site-Specific Poly(ethylene glycol)ylation of Peptides," In ACS Symposium Series 680 Poly(Ethylene Glycol) Chemistry: Chemistry and Biological Applications. Plenum Press. Washington D.C.: pp. 218-238 (1997).

Hale et al., "Improving the Outcome of Bone Marrow Transplantation by Using CD52 Monoclonal Antibodies to Prevent Graft-Versus-Host Disease and Graft Rejection," *Blood* 92: 4581-4590 (1998).

Hargreaves et al, "Selective Depletion of Activated T Cells: the CD40L-Specific Antibody Experience," *Trends in Molecular Medicine* 10:130-135 (2004).

Hellstrom et al., "Chapter 15: Antibodies for Drug Delivery," Controlled Drug Delivery: Fundamentals and Applications. $2^{nd}$ ed. New York and Basel. pp. 623-653 (1987).

Hudson et al., "Engineered Antibodies," *Nat Med.* 9: 129-134 (2003).

Hutloff et al., "ICOS is an Inducible T-Cell Co-Stimulator Structurally and Functionally Related to CD28," *Nature* 397:263-266 (1999).

Isaacs, "From Bench to Bedside: Discovering Rules for Antibody Design, and Improving Serotherapy with Monoclonal Antibodies," *Rheumatology* 40:724-738 (2001).

Iwai et al., "Involvement of Inducible Costimulator-B7 Homologous Protein Costimulatory Pathway in Murine Lupus Nephritis," *J Immunol.* 171:2848-2854 (2003).

Kettleborough et al., "Isolation of Tumor Cell-Specific Single-Chain Fv from Immunized Mice Using Phage-Antibody Libraries and the Re-Construction of Whole Antibodies from These Antibody Fragments," *Eur J Immunol.* 24:952-958 (1994).

Kohler et al., "Continuous Cultures of Fused Cells Secreting Antibody of Predefined Specificity," *Nature* 256:495-497 (1975).

Kozbor et al., "The Production of Monoclonal Antibodies from Human Lymphocytes," *Immunol Today* 4: 72-79 (1983).

Ling et al., "Cutting Edge: Identification of GL50, a Novel B7-Like Protein That Functionally Binds to ICOS Receptor," *J Immunol.* 164:1653-1657 (2000).

Lohning et al., "Expression of ICOS in Vivo Defines CD4+ Effector T Cells with High Inflammatory Potential and a Strong Bias for Secretion of Interleukin 10," *J Exp Med.* 197: 181-193 (2003).

Mages, "Molecular Cloning and Characterization of Murine ICOS and Identification of B7h as ICOS Ligand," *Eur J Immunol.* 30:1040-1047 (2000).

Miletic et al., "Complement-Immunoglobulin Interactions," *Curr Opin Immunol.* 7:41-47 (1995).

Milstein et al., "Hybrid Hybridomas and Their Use in Immunohistochemistry," *Nature* 305:537-540 (1983).

Moore et al., "To Affinity and Beyond," *Nature* 426:725-731, 2003.

Ozkaynak et al., "Importance of ICOS-B7RP-I Costimulation in Acute and Chronic Allograft Rejection," *Nat Immunol.* 2:591-596 (2001).

Persic et al., "An Integrated Vector System for the Eukaryotic Expression of Antibodies or Their Fragments After Selection from Phage Display Libraries," *Gene* 187:9-18 (1997).

Sakamoto et al, "AILIM/ICOS: Its Expression and Functional Analysis with Monoclonal Antibodies," *Hybrid Hybridomics* 20: 293-303 (2001).

Skerra, "Engineered Protein Scaffolds for Molecular Recognition," *J Mol Recognit.* 13:167-187 (2000).

Skerra, "Lipocalins as a Scaffold," *Biochim Biophys Acta.* 1482:337-350 (2000).

Sporici et al, "ICOS Ligand Costimulation is Required for T-Cell Encephalitogenicity," *Clin Immunol.* 100: 277-288 (2001).

Tan, "Autoantibodies and Autoimmunity: A Three-Decade Perspective," *Ann NY Acad Sci.* 815:1-14 (1997).

Thorpe et al., "The Preparation and Cytotoxic Properties of Antibody-Toxin Conjugates," *Immunol Rev* 62:119-158 (1982).

Totsuka et al., "Ameliorating Effect of Anti-inducible Costimulator Monoclonal Antibody in a Murine Model of Chronic Colitis," *Gastroenterology* 124:410-421 (2003).

Traunecker et al., "Bispecific Single Chain Molecules (Janusins) Target Cytotoxic Lymphocytes on HIV Infected Cells," *EMBO J.* 10: 3655-3659 (1991).

Uchida et al., "The Innate Mononuclear Phagocyte Network Depletes B Lymphocytes Through Fc Receptor-Dependent Mechanisms During Anti-CD20 Antibody Immunotherapy," *J Exp Med.* 199(12): 1659-1669 (2004).

Van de Winkel et al., "Introduction: Human IgG Fc Receptors," Molecular Biology Intelligence Unit. Austin, TX: pp. 1-3., 1996.

Yoshinaga et al., "T-Cell Co-Stimulation Through B7RP-1 and ICOS," *Nature* 402:827-832 (1999).

Yu et al., "CD28 Signal Enhances Apoptosis of CD8 T Cells After Strong TCR Ligation," *J Immunol.* 170:3002-3006 (2003).

Zalipsky et al., "Chapter 21: Use of Functionalized Poly(Ethylene Glycol)s for Modification of Polypeptides," Poly(Ethylene Glycol) Chemistry: Biotechnical and Biomedical Applications. Plenum Press. New York : pp. 347-370 (1992).

Barbey et al., "DEL Cell Line: A 'Malignant Histiocytosis' CD30+ t(5;6)(q35;p21) Cell Line," *Int. J. Cancer* 45:546-553 (1990).

Blazar et al., "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," *J. Immunol.* 157:3250-3259 (1996).

Buonfiglio et al., "The T Cell Activation Molecule H4 and the CD28-Like Molecule ICOS are Identical," *Eur. J. Immunol.* 30:3463-3467 (2000).

Chambers et al., "Co-Stimulation in T Cell Responses," *Curr. Opin. Immunol.* 9:396-404 (1997).

CRL 8001 ATCC Cell Lines and Hybridomas, p. 393, 8$^{th}$ edition, 1994 American Type Culture Collection catalog.

Dianzani et al., "Characterization of Human H4, A Novel Surface Molecule Selectively Expressed by Activated T Cells and Mature Thymocytes," *FASEB J.* 13:719.39 Abstract #712.39 (1999).

Fischer et al., "A Ki-1 (CD30)-Positive Human Cell Line (Karpas 299) Established From a High-Grade Non-Hodgkin's Lymphoma, Showing a 2;5 Translocation and Rearrangement of the T-Cell Receptor Beta-Chain Gene," *Blood* 72:234-240 (1988).

Freeman et al., "Coning of B7-2: A CTLA-4 Counter-Receptor That Costimulates Human T Cell Proliferation," *Science* 262:909-911 (1993).

Futamatsu et al., "Attenuation of Experimental Autoimmune Myocarditis by Blocking Activated T Cells Through Inducible Costimulatory Molecule Pathway," *Cardiovasc. Res.* 59:95-104 (2003).

Gonzalo et al., "ICOS is Critical for T Helper Cell-Mediated Lung Mucosal Inflammatory Responses," *Nat. Immunol.* 2:597-604 (2001).

Greenfield et al., "CD28/B7 Costimulation: A Review," *Crit. Rev. Immunol.* 18:389-418 (1998).

Groettrup et al., "A Third Interferon-Gamma-Induced Subunit Exchange in the 20S Proteasome," *Eur. J. Immunol.* 26:863-869 (1996).

Hara et al., "Human T Cell Activation. II. A New Activation Pathway Used by a Major T Cell Population Via A Disulfide-Bonded Dimer of A 44 Kilodalton Polypeptide (9.3 Antigen)," *J. Exp. Med.* 161:1513-1524 (1985).

Harada et al., "The Role of the ICOS-B7h T Cell Costimulatory Pathway in Transplantation Immunity," *J. Clin. Invest.* 112:234-243 (2003).

Iwai et al., "Amelioration of Collagen-Induced Arthritis by Blockade of Inducible Costimulator-B7 Homologous Protein Costimulation," *J. Immunol.* 169:4332-4339 (2002).

Kanai et al., "ICOS Costimulation in Inflammatory Bowel Disease," *J. Gastroenterol.* 37:78-81 (2002).

Keane-Myers et al., "Development of Murine Allergic Asthma is Dependent Upon B7-2 Costimulation," *J. Immunol.* 160:1036-1043 (1998).

Kirk et al., "CTLA4-Ig and Anti-CD40 Ligand Prevent Renal Allograft Rejection in Primates," *Proc. Natl. Acad. Sci. USA* 94:8789-8794 (1997).

Lanier et al., "CD80 (B7) and CD86 (B70) Provide Similar Costimulatory Signals for T Cell Proliferation, Cytokine Production, and Generation of CTL," *J. Immunol.* 154:97-105 (1995).

Lee et al., "Increased Vaccine-Specific T Cell Frequency After Peptide-Based Vaccination Correlates With Increased Susceptibility to In Vitro Stimulation But Does Not Lead to Tumor Regression," *J. Immunol.* 163:6292-6300 (1999).

Lenschow et al., "CD28/B7 System of T Cell Costimulation," *Annu. Rev. Immunol.* 14:233-258 (1996).

Linsley et al., "Coexpression and Functional Cooperation of CTLA-4 and CD28 on Activated T Lymphocytes," *J. Exp. Med.* 176:1595-1604 (1992).

Liu et al., "B7H Costimulates Clonal Expansion of, and Cognate Destruction of Tumor Cells by, CD8(+) T Lymphocytes In Vivo," *J. Exp. Med.* 194:1339-1348 (2001).

Lucas et al., "Naive CD28-Deficient T Cells Can Initiate but not Sustain an In Vitro Antigen-Specific Immune Response," *J. Immunol.* 154:5757-5768 (1995).

Lucia et al., "Expression of the Novel T Cell Activation Molecule hpH4 in HIV-Infected Patients: Correlation With Disease Status," *AIDS Res. Hum. Retroviruses* 16:549-557 (2000).

Mathur et al., "CD28 Interactions With Either CD80 or CD86 Are Sufficient to Induce Allergic Airway Inflammation in Mice," *Am. J. Respir. Cell Mol. Biol.* 21:498-509 (1999).

Matsui et al., "Adenovirus-Mediated Gene Transfer of ICOSIg Fusion Protein Ameliorates Ongoing Experimental Autoimmune Myocarditis," *Hum. Gene Ther.* 14:521-532 (2003).

Nakamura et al., "Acceptance of Islet Allografts in the Liver of Mice by Blockade of an Inducible Costimulator," *Transplantation* 75:1115-1118 (2003).

Nanji et al., "Costimulation Blockade of Both Inducible Costimulator and CD40 Ligand Induces Dominant Tolerance to Islet Allografts and Prevents Spontaneous Autoimmune Diabetes in the NOD Mouse," *Diabetes* 55:27-33 (2006).

Nielsen et al., "Melanoma Vaccines: The Paradox of T Cell Activation Without Clinical Response," *Cancer Chemother. Pharmacol.* 46:S62-S66 (2000).

Nishioka et al., "The Role of CD40-CD40 Ligand Interaction in Human T Cell-B Cell Collaboration," *J. Immunol.* 153:1027-1036 (1994).

Nurieva et al., "Inducible Costimulator is Essential for Collagen-Induced Arthritis," *J. Clin. Invest.* 111:701-706 (2003).

Okamoto et al., "Expression and Function of the Co-Stimulator H4/ICOS on Activated T Cells of Patients With Rheumatoid Arthritis," *J. Rheumatol.* 30:1157-1163 (2003).

Redoglia et al., "Characterization of H4: A Mouse T Lymphocyte Activation Molecule Functionally Associated With the CD3/T Cell Receptor," *Eur. J. Immunol.* 26:2781-2789 (1996).

Riley et al., "Intrinsic Resistance to T Cell Infection With HIV Type 1 Induced by CD28 Costimulation," *J. Immunol.* 158:5545-5553 (1997).

Rottman et al., "The Costimulatory Molecule ICOS Plays an Important Role in the Immunopathogenesis of EAE," *Nat. lmmunol.* 2:605-611 (2001).

Sato et al., "Hyperexpression of Inducible Costimulator and Its Contribution on Lamina Propria T Cells in Inflammatory Bowel Disease," *Gastroenterology* 126:829-839 (2004).

Shahinian et al., "Differential T Cell Costimulatory Requirements in CD28-Deficient Mice," *Science* 261:609-612 (1993).

Tamatani and Tezuka, "Human Cell Surface Protein," Genseq. Database Accession No. W75956, Dec. 11, 1998.

Tamatani and Tezuka, "Human Cell Surface Protein," Genseq. Database Accession No. V53199, Dec. 11, 1998.

Wallin et al., "Enhancement of CD8+ T Cell Responses by ICOS/B7h Costimulation," *J. Immunol.* 167:132-139 (2001).

Wills-Karp et al., "Murine Models of Asthma in Understanding Immune Dysregulation in Human Asthma," *Immunopharmacology* 48:263-268 (2000).

Van Regenmortel et al., "Mapping Epitope Structure and Activity: From One-Dimensional Prediction to Four-Dimensional Description of Antigenic Specificity," *Methods*. 9:465-472 (1996).

Zuberek et al., "Comparable in Vivo Efficacy of CD28/B7, ICOS/GL50, and ICOS/GL50B Costimulatory Pathways in Murine Tumor Models: IFNgamma-Dependent Enhancement of CTL Priming, Effector Functions, and Tumor Specific Memory CTL," *Cell. Immunol.* 225:53-63 (2003).

International Search Report for PCT/DE98/02896 dated Mar. 23, 1999.

Interference No. 105, 168, Judgment Board of Appeals entered Jun. 21, 2005.

Ogawa et al., "Opposing Effects of Anti-Activation-Inducible Lymphocyte-Immunomodulatory Molecule/Inducible Costimulator Antibody on the Development of Acute Versus Chronic Graft-Versus-Host Disease," *J. Immunol.* 167: 5741-5748 (2001).

European Patent Office Communication for EP05737106.4 dated Oct. 12, 2010.

* cited by examiner

ANTIBODIES FOR DEPLETION OF ICOS-POSITIVE CELLS IN VIVO

CROSS REFERENCE TO RELATED APPLICATIONS

This application is the U.S. National Stage of International Application No. PCT/EP2005/004349, filed Apr. 22, 2005 which claims the benefit of U.S. Provisional Application No. 60/581,479, filed Jun. 21, 2004, and European Patent Application No. 04009659.6, filed Apr. 23, 2004, all hereby incorporated by reference.

BACKGROUND OF THE INVENTION

The present invention relates generally to binding agents useful in the selective depletion of T cells in vivo. More specifically, the invention relates to ICOS-binding agents which once bound to ICOS expressed on the surface of cells, in particular ICOS-bearing T cells, result in the in vivo depletion of cells to which they are bound. Methods of treating T cell related diseases using said ICOS-binding agents, pharmaceutical compositions comprising said ICOS-binding agents, a method of identifying an ICOS-binding agent, and monoclonal anti-ICOS antibodies capable of in vivo eliminating cells which express ICOS on their surface are also provided.

The concept of depleting T cells in autoimmune disease and transplantation is not new and has successfully been practiced in the clinic for decades (Hargreaves R E G, Trends in Molecular Medicine 2004; 10:130-135). However, the antigens which were targeted on T cells (CD3, CD4, CD52) are all broadly expressed on resting and activated T cells or even on other cell types. Therefore, the existing therapeutic regimens are broadly immunosuppressive. The depletion of activated T cells expressing ICOS in vivo, as described in the present invention, offers much higher specificity of the therapeutic effect, since ICOS is only significantly expressed on activated effector T cells (Löhning M, Journal of Experimental Medicine 2003; 197:181-193; Bonhagen K, European Journal of Immunology 2003; 33:392-401).

In the European Patent Application EP1 158 004 A2 human antibodies are described, which can kill ICOS-overexpressing transfectants in vitro based on the mechanism of Antibody Dependent Cell-mediated Cytotoxicity (ADCC) with human peripheral blood lymphocytes. The described experiment demonstrates that the used antibodies can mediate a certain type of in vitro cytotoxicity but does not provide any information whether ICOS-expressing T cells can at all be depleted in vivo. There are a number of reasons, why this experiment cannot provide this information: 1. ICOS overexpressing transfected lines were used as targets and not normal T cells with physiological ICOS expression. 2. ADCC as used in the described experiment has often been demonstrated as a cell-depleting mechanism in vitro, but has been largely excluded as a mechanism of for cell depletion in vivo (Alters S E, Journal of Immunology 1990; 144:4587-4592; Uchida J, Journal of Experimental Medicine 2004; 199:1659-1669). ADCC will work in vitro with any antibody capable of binding to a surface molecule having the right isotype to be recognized by the cytotoxic cells in vitro. 3. There are a variety of additional reasons (see below), why in vitro depletion tests in general have no predictive value for in vivo depletion (Uchida J, Journal of Experimental Medicine 2004; 199: 1659-1669, Isaacs J D, Rheumatology 2001; 40:724-738). This is the reason why it has been difficult to generate in vivo depleting antibodies directed against other T cell surface activation antigens like CTLA-4 or OX40, whereas in vitro (e.g. ADCC-based) T cell-depletion against these targets will work fine (Hargreaves R E G, Trends in Molecular Medicine 2004; 10:130-135).

A greater number of factors are important in determining whether a given cell surface molecule can be used as a target for cell depletion in vivo: level of target molecule cell surface expression, target antigen valency, distribution of the targeted antigen on the cell surface, its proximity to the cell membrane, occurrence or not of internalization of the target molecule after antibody binding, course and duration of physiological expression, accessibility of the target antigen in various tissues (lymph nodes, spleen, blood), and other factors (Alters S E, Journal of Immunology 1990; 144:4587-4592; Uchida J, Journal of Experimental Medicine 2004; 199:1659-1669; Isaacs J D, Rheumatology 2001; 40:724-738). These factors and thus the general usefulness of a given molecule as a target for cell depletion can only be tested using an appropriate model in vivo.

Moreover, ICOS as a co-stimulatory molecule poses the danger that antibodies or other agents directed to ICOS lead instead of depletion to an untoward activation and expansion of ICOS$^+$ T cells in vivo with potentially severe disease-aggravating effects. Up to date there are no data available whether T cells can be depleted in vivo using a co-stimulatory molecule as a target. In vitro tests for ICOS co-stimulatory effects do not have a predictive value for the in vivo situation, since many critical parameters cannot be correctly reproduced in vitro (e.g. ICOS surface density and surface distribution, binding characteristics of the ICOS-binding agents to various tissues, etc.). Therefore, the question whether ICOS can be used as a target for a therapeutic depletion of activated T cells in vivo without adverse cell activation and proliferation can only be answered in an appropriate disease model in vivo. Only such an in vivo test has a predictive capacity for the usefulness of ICOS as therapeutic target. At the same time, only in vivo tests have a predictive value for the usefulness of monoclonal antibodies directed to ICOS as depleting agents.

DETAILED DESCRIPTION

In the present invention it is described that it is possible to deplete ICOS-expressing T cells in vivo without adverse reactions (e.g. cell activation, proliferation, expansion of ICOS-expressing T-cells) in a model of lung allergy with the use of monoclonal antibodies. It is further demonstrated that it is possible to attenuate the model disease by depleting ICOS$^+$ cell in vivo.

The immune system is composed of various highly specialized cell types, among them T lymphocytes. Physiologically, T lymphocytes circulate in the body in a resting state. Under these circumstances the T cells express on their surface the T cell receptor, which is responsible for the recognition of antigen. In addition to the T cell receptor, resting T lymphocytes express a number of other cell surface molecules in a constitutive fashion. Some of these surface proteins are responsible for the adequate migration of the T cells through body compartments, some provide binding forces ("adhesion") to other cells of the immune system, some are expressed to ensure appropriate activation of T cells once these recognize their antigen (e.g. CD4, CD8, CD3, CD28). As long as the T cells patrolling the various body compartments do not encounter an antigen to which their T cell receptor is directed, they remain quiescent and do not change their pattern of cell surface molecules. Once T cells encounter antigen presented by "antigen-presenting cells" (e.g. dendritic cells), T cells become partially activated. Recognition of the antigen by the T cell receptor alone is in most cases insufficient for full activation of T lymphocytes, which usually requires the simultaneous stimulation by additional T cell surface molecules (also called "co-stimulators" or "co-stimulatory molecules" hereinafter). Following activation by antigen, T cells start to express a number of new cell surface molecules (e.g. CD25, CD69), among them also new co-stimulatory molecules (e.g. ICOS, OX-40, 4-1BB, (Carreno B et al., Annu. Rev. Immunol. 2002, 20:29-53; Croft M, Nat. Rev. Immunol. 2003, 3: 609-620)). The activated T cells also start to proliferate and begin to synthesize numerous cytokines, e.g. IL-2 and IFN-γ, which function as messengers. T cell activation is thus not a single step process but consists of an initial activation followed by consecutive steps of ongoing T cell activation and differentiation. The end-point of this activation process are "effector T cells", which are fully activated and armed T cells capable of exerting a variety of effector functions. Typical effector functions are: a) synthesis and secretion of cytotoxic substances (employed to "kill" other cells), b) communication with other cells of the immune system via T cell surface molecules or via secreted cytokines. Through these effector functions T cells direct the antigen-specific immune response. Effector T cells accumulate at the site of pathogen invasion and are capable of eliminating infected cells by releasing cytotoxic substances. Effector T cells also induce inflammation and direct and control the generation of antigen-specific antibodies by B cells. In the physiological immune defense, cytotoxic cells, as well as the specifically formed antibodies, eliminate viral or bacterial pathogens which have invaded the body. Once the pathogen is cleared, the T cells which have participated in the immune defense against this pathogen physiologically either die or are transformed to "memory" T cells.

Under certain circumstances, however, the immune system does not return to a quiescent state. One type of malfunction is an overreaction towards the pathogen. In that case antigen-specific T cells become very strongly activated by the invading pathogen and this results in an extremely strong killing of body cells infected by the pathogen (virus, bacteria). An example of this type of aberrant reaction would be the fulminant hapatic failure observed in some cases of infection with hepatitis B virus. In this situation, the majority of hepatic cells are infected by the hepatitis B virus. The host mounts an overtly strong immune response and develops many cytotoxic T cells recognizing hepatitis B viral antigens. As a result, the majority of the host hepatic cells are killed in the T cell effector phase, largely depleting the patient of functional hepatic cells and leading to a life-threatening liver failure.

Another type of malfunction of the immune system is the autoimmune reaction. The starting trigger of autoimmune reactions is largely unknown and may be originally an infection. Whatever the original cause, the common feature of autoimmune conditions is that the immune system aberrantly recognizes self-antigens as "foreign" and thus turns the immune defenses (T cells, B cells) against the body's own tissues. Depending on the tissue type recognized as "foreign" by the immune system various clinical pictures arise. Clinically well characterized "autoimmune diseases" are for example rheumatoid arthritis, ankylosing spondylitis, Sjögren's syndrome, inflammatory bowel diseases (colitis ulcerosa, Crohn's disease), multiple sclerosis, sarcoidosis, psoriasis, systemic lupus erythematosus, vasculitis, and others. In all of these diseases T cells either directly attack the host's own tissue or instruct B cells to generate disease-causing self-reactive antibodies (Tan E M, Ann NY Acad Sci 1997, 815:1-14). In all cases of autoimmune reactions effector T cells accumulate in the attacked tissues.

Another type of malfunction of the immune system is the allergic reaction. Physiologically, the immune system is designed to recognize antigens from foreign pathogens which pose a danger to the host. In contrast, foreign antigens which do not pose a danger to the host are ignored. To this group of non-dangerous foreign antigens belong many environmental antigens, e.g. pollen, food antigens or bee venoms. The immune system of an allergic host aberrantly recognizes these environmental antigens and reacts to them by generating T cell effectors against these environmental antigens. At the same time, the host reacts by activating its B cell immune system against these antigens. Again, the B cell allergic reaction is directed and controlled by effector T cells. As a result of this aberrant recognition of environmental antigens, and depending on the type of antigen recognized, allergic individuals suffer from a variety of conditions. One major disease entity is the allergic asthma of the lung, in which inhaled foreign proteins are aberrantly recognized by the immune system (often tree and grass pollen), leading to an inflammation of lung tissue and development of an antibody response against the antigen (often of the IgE isotype). Allergic reactions can be triggered by food components, resulting often in acute life-threatening conditions. Life-threatening conditions can also arise from allergy against bee venoms.

Unwanted reactions of the T cell and B cell immune system are also encountered following allogeneic tissue transplantations. The host receives either an organ from the donor or he receives hematopoietic cells (e.g. stem cells, bone marrow) from which immune cells arise. In the first instance the host often recognizes the organ as foreign and mounts an immune defense (effector T cells, humoral B cell response directed by effector T cells) against the foreign tissue ("organ rejection"). In the second instance the transplanted foreign stem cell or bone marrow cells can mount an immune attack against the host. This immune attack leads to a "graft-versus host disease". The organ rejection or the graft-versus host disease can be prevented by suppressing and/or eliminating the involved host or graft effector T cells (Hale G et al., Blood 1998, 92:4581-4590).

Cancer diseases are characterized by unrepressed continuous growth of the body's own cells. In some cases cells of the immune system are affected by this uncontrolled expansion and these conditions are termed lymphomas. T cell lymphomas characteristically express T cell surface activation antigens and they resemble in that respect activated T cells.

Physiological immune reactions involving T cells and directed against invading pathogens but also pathological inflammatory processes in the course of autoimmune diseases (for a non-limiting list of diseases see above), chronic allergy reactions (for a non-limiting list of diseases see above) or transplantation reactions (comprising organ rejection, graft-versus-host disease) all lead to the accumulation of activated antigen-specific effector T cells at the site of the immune reaction.

Immune therapies employed to date are relatively unspecific. Pharmacological immuno-suppressants like steroid compounds, Cyclosporine A or Rapamycin exert their action in a very broad fashion and effect many cells of the immune system. Thus the application of these immunosuppressants render the recipient severely immunocompromised leading to many unwanted side effects. At the same time, these agents act only as long as they are applied, since they suppress activation of T cells but do not eliminate T cells. In consequence, once this type of immunosuppressive agent is withdrawn, T cells with an appropriate T cell receptor will recognize the autoantigen or allergen and the unwanted immune reaction will restart.

An alternative method of treatment is the use of monoclonal or polyclonal antibodies for permanent elimination of certain T cells. After binding of the antibody the T cells are to removed from the circulation and permanently destroyed. Treatment with monoclonal antibodies (mAb) directed to the T-cell surface molecule CD3 has been employed in the past (Brock M V et al., J. Heart Lung Transplant. 2001, 20:1282-1290). This type of treatment, however, eliminates the entire T cell population and leaves the patient severely immunocompromised and hence highly susceptible to infection. A preferable approach would be to selectively remove only those T cells that are actively involved in the autoimmune/allergic/inflammatory/rejection response, leaving the remaining T cell population intact. This method of treatment has not yet been achieved.

ICOS is a co-stimulatory molecule with unusual expression characteristics. It is not expressed on resting T cells (e.g. naïve T cells, quiescent memory T cells) but is de novo expressed on the cell surface after T cell activation in vivo and remains on the cell surface throughout the entire T cell effector phase (Bonhagen K et al., Eur J. Immunol. 2003, 33:392-410). It is not expressed on other cells of the immune system such as B cells, dendritic cells or macrophages (Hutloff et al., Nature 1999, 397:263-266). ICOS physiologically interacts with another cell surface molecule, the ICOS-Ligand (ICOS-L), which is expressed on a variety of cells in the body (Carreno B et al., Annu. Rev. Immunol. 2002, 20:29-53). Engagement and crosslinking of ICOS by its natural ligand in the presence of antigen physiologically augments all T cell effector functions (e.g. proliferation, secretion of cytokines and cytotoxic molecules, upregulation of cell surface molecules (Yoshinaga S K et al., Nature 1999, 402:827-832). Overexpression of ICOS-L in vivo, however, leads to a stimulation of T cells that results in a pathological expansion of plasma cells and a functional breakdown of the immune system (Yoshinaga S K et al., Nature 1999, 402:827-832). In vitro, the co-stimulation of all T cell functions can also be observed after engagement of ICOS by ICOS-specific antibodies, which crosslink ICOS on the cell surface (Hutloff et al., Nature 1999, 397:263-266). Based on these data, engagement of ICOS by monoclonal or polyclonal antibodies is therefore likely to trigger an undesired co-stimulatory activation and expansion of ICOS-positive T cells in vivo (see also Example 4), with many untoward effects.

We have now found that it is possible to isolate ICOS-binding agents which cause the in vivo depletion of T cells to which they are bound. The present invention therefore provides a method of specifically depleting effector T cells driving an undesired immune reaction.

The invention has many advantages over existing therapy modes. Only T cells recognizing the unwanted autoimmune/allergic/inflammation/transplantation antigen are very specifically and permanently removed from the immune system and the beneficial effect continues after cessation of the treatment. Treated individuals will remain fully immunocompetent against infectious pathogens. Since these effector T cells also direct the generation of antigen-specific B cells and thus govern the secretion of antigen-specific antibodies, the removal of antigen-specific effector T cells may also lead to a suppression of the antigen-specific B cell response. Thus the depletion of ICOS-positive cells from the immune system represents a major advancement in the treatment of many conditions with unwanted immune reactions. For the purpose of the present invention, ICOS-positive cells (ICOS-positive cells) are understood to comprise any cells expressing ICOS on the cell surface, in particular T cells, preferably activated T cells.

A first aspect of the present invention refers to an ICOS-binding agent, wherein said agent once bound to ICOS expressed on the surface of cells, preferably on ICOS-bearing activated T cells, results in the in vivo depletion of the cells to which it is bound.

The term "depletion" as used in the present invention refers to the partial or preferably total removal of ICOS-positive cells from the immune system. Hence the ICOS-binding agents of the present invention may be any agent capable of binding to ICOS and capable of partially or preferably totally removing ICOS-positive cells from the immune system. Preferably, depletion of ICOS-positive cells refers to a therapeutically effective depletion of cells expressing ICOS on the cell surface from the immune system, preferably of activated ICOS-positive T cells.

The therapeutically effective depletion of ICOS-positive cells may lead to a reduction of activated T cells in an individual suffering from an overreaction towards a pathogen, an autoimmune disease, an inflammatory disease, an allergic reaction, a graft-versus-host disease or a T cell lymphoma. Preferably, the therapeutically effective depletion of ICOS-positive cells leads to a therapeutic effect in the aforementioned aberrant or inappropriate immune reactions. A therapeutically effective depletion may be detected by observing a reduction in the total number of ICOS positive cells in vivo, in particular in a blood or tissue sample obtained from a patient, or by the suppression of aberrant or inappropriate immune reactions. The depletion of ICOS-positive cells may be detected for example by using the methods described in the examples herein or by any other suitable method known in the art (e.g. histology).

The ICOS-binding agent preferably comprises an ICOS-binding peptide or protein capable of binding to ICOS expressed on the surface of cells, preferably ICOS-bearing activated T cells, wherein the binding results in the in vivo depletion of the cells to which the ICOS-binding peptide or protein has bound. Preferably the ICOS-binding agent binds human ICOS and depletes human cells expressing ICOS on their surface, in particular activated T cells, in vivo, in particular without adverse cell activation, proliferation or expression of ICOS-expressing T cells.

As used herein, the terms "binding protein" or "binding peptide" refer to a class of proteins or peptides which bind to ICOS expressed on the surfaces of cells and deplete ICOS bearing cells to which they are bound, in particular ICOS bearing activated T cells, in a therapeutically effective way including, without limitation, polyclonal or monoclonal antibodies, antibody fragments and protein scaffolds directed against ICOS, e.g. anticalins which are directed against ICOS. The therapeutic effectiveness of the depletion of ICOS-positive T cells may be directly assessed by monitoring the levels of ICOS-positive T cells in the circulation or in the affected tissues, and indirectly e.g. by measuring parameters of local or systemic inflammation, by determining autoantibody levels or by testing the organ function.

In preferred embodiments of the invention the ICOS-binding peptide or protein is an antibody or fragment thereof, which binds to ICOS expressed on the surface of cells, preferably ICOS-bearing activated T cells, wherein the binding results in the in vivo depletion of the cells to which the anti-ICOS antibody or fragment thereof is bound. The procedure for preparing an antibody or antibody fragment is preferably effected using either the standard hybridoma technique (see e.g. Example 1) or in accordance with any of the recombinant methods well known to the skilled person (Technology Feature, Nature 2003, 426:725-731; Hudson P J, Nat. Medicine 2003, 9:129-134).

Herein, the term antibody or antibody fragment is also understood as meaning antibodies, antibody fragments, or antigen-binding parts thereof, in particular complementarity-determining regions (CDRs) of antibodies, which have been prepared recombinantly and, where appropriate, modified, such as chimaeric antibodies, humanized antibodies, multi-functional antibodies, bispecific or oligospecific antibodies, single-chain antibodies and Fab, Fab' or F(ab)$_2$ fragments (see, for example, EP-B1-0 368 684, U.S. Pat. No. 4,816,567, U.S. Pat. No. 4,816,397, WO 88/01649, WO 93/06213 or WO 98/24884), fragments produced by a Fab expression library, anti-idiotypic (anti-Id) antibodies, and epitope-binding fragments of any of the above.

As an alternative to the classical antibodies it is also possible, for example, to use protein scaffolds against ICOS, e.g. anticalins which are based on lipocalin (Beste et al. (1999) Proc. Natl. Acad. Sci. USA, 96, 1898-1903). The natural ligand-binding sites of the lipocalins, for example the retinol-binding protein or the bilin-binding protein, can be altered, for example by means of a "combinatorial protein design" approach, in such a way that they bind to selected haptens, here to ICOS (Skerra, 2000, Biochim. Biophys. Acta, 1482, 337-50). Other known protein scaffolds are known as being alternatives to antibodies for molecular recognition (Skerra (2000) J. Mol. Recognit., 13, 167-187).

In an advantageous embodiment of the present invention the ICOS-binding agent comprises an anti-ICOS antibody or fragment thereof which depletes the bound ICOS-positive cells through attraction and activation of complement. Activated complement then kills the cells through its cytotoxic action. Alternatively, the ICOS-positive cells may be depleted by phagocytic cells which engage the bound anti-ICOS antibody or fragment thereof through their Fc receptors and thus receive a signal to phagocytose the antibody-marked cell in vivo.

The antibodies and antibody fragments which mediate the removal of ICOS-positive cells are also called anti-ICOS antibodies or anti-ICOS antibody fragments, herein. The ICOS-binding agents which deplete ICOS-positive cells in vivo may also be identified using a method of the present invention of screening an ICOS-binding agent.

Also provided by the present invention are is the monoclonal antibody MIC-944 which is produced by the hybridoma MIC-944, which has been deposited by the applicant on Apr. 14, 2004 at the Deutsche Sammlung von Mikroorganismen and Zellkulturen GmbH (DSMZ) at Mascheroder Web 1b, D-38124, Braunschweig, Germany, under the accession number DSM ACC 2645, and the monoclonal antibody 9F3 produced by the hybridoma 9F3, which has been deposited by the applicant on Apr. 14, 2004 at the DSMZ under the accession number DCM ACC 2646. These antibodies bind mouse ICOS and have been demonstrated to in vivo deplete mouse T cells bearing ICOS on their surface (See Examples 1, 3, 4, and 5 herein).

In one embodiment the ICOS-binding agents of the present invention which bind human ICOS deplete human ICOS-positive cells in a comparable way to the depletion of mouse ICOS-positive cells by monoclonal antibodies MIC-944 and/or 9F3.

In one embodiment, the ICOS-binding agent is an antibody or an antigen binding fragment thereof which has an epitopic specificity for human ICOS similar to that of the monoclonal antibodies MIC-944 and/or 9F3 for mouse ICOS and includes antibodies or antigen binding fragments reactive with the same or a functionally equivalent epitope on human ICOS as the mouse ICOS epitope bound by the monoclonal antibodies MIC-944 and/or 9F3.

The term epitope is meant to refer to that portion of the antigen capable of being recognized by and bound by an antibody. Epitopes usually consist of chemically active surface groupings of molecules such as amino acids or sugar side chains and have specific three dimensional structural characteristics as well as specific charge characteristics. The ICOS epitope bound by ICOS-binding agents of the present invention is preferably one which does not result in co-stimulation of ICOS and instead allows ICOS bearing cells to be depleted by the ICOS-binding agent in vivo.

Consequently, a functionally equivalent epitope is an epitope which when bound by ICOS-binding agents of the present invention is preferably one which does not result in co-stimulation of ICOS and instead allows ICOS bearing cells to be in vivo depleted by the ICOS-binding agent, e.g. the epitope on human ICOS or on mouse ICOS, such as the epitope on mouse ICOS recognized by the antibodies MIC-944 and/or 9F3.

In the case of species conserved epitopes screening of ICOS-binding agents can be carried out utilizing a competition assay. If the ICOS-binding agent being tested competes with one of the monoclonal antibodies MIC-944 or 9F3 then it is likely that the ICOS-binding agent binds to the same, or a closely related epitope. Still another way to determine whether an agent has the specificity of the monoclonal antibodies MIC-944 and/or 9F3 described herein is to pre-incubate one of these monoclonal antibodies with ICOS and allow it to bind, then add the agent being tested to determine if the agent being tested is inhibited in its ability to bind ICOS. If it is then, in all likelihood, it has the same or a functionally equivalent epitope binding specificity as the anti-ICOS monoclonal antibodies MIC-944 or 9F3 described herein.

Advantageously, the ICOS-specific antibodies may be engineered for optimal binding of complement, by using chimeric antibodies with a suitable IgG heavy chain, in which the complement-binding region has been optionally mutated for maximal binding of complement components according to standard methods (Miletic V D et al., Curr. Opin. Immunol. 1995, 7:41-47).

In another embodiment the ICOS-specific antibodies may be engineered for optimal binding to Fc receptor of phagocytic cells according to standard methods (F. Shakib (Ed.), The human IgG subclasses, Pergamon Press 1990; Winkel J G van de, Capel P J (Eds.), Human IgGFc receptors, Springer 1996), so that optimal in vivo depletion results.

Antibodies include immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD and IgA) or subclass of immunoglobulin molecule.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

The antibodies or fragments thereof for use in the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15):7843-7848 and in WO92/02551.

Humanized antibodies are preferably antibody molecules from non-human species having one or more complementarity determining regions (CDRs) from the non-human species and a framework region from a human immunoglobulin molecule (see, e.g. U.S. Pat. No. 5,585,089).

Chimeric antibodies preferably are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al., 1983, Nature 305:537-539; WO 93/08829, Traunecker et al., 1991, EMBO J. 10:3655-3659). Multi-valent antibodies may comprise multiple specificities or may be monospecific (see for example WO 92/22853).

The antibodies for use in the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. Techniques for the production of single chain antibodies, such as those described in U.S. Pat. No. 4,946,778 can also be adapted to produce single chain antibodies to ICOS. Also, transgenic mice, or other organisms, including other mammals, may be used to express humanized antibodies.

In another preferred embodiment of the present invention the ICOS-binding agent comprises an ICOS-binding component conjugated to one or more effector molecule(s). Examples of suitable ICOS-binding components preferably comprise anti-ICOS antibodies and fragments thereof as described herein above, and ICOS-L and fragments thereof.

In one example, the ICOS-binding component for use in the ICOS-binding agent of the present invention may comprise all or part of the ICOS-L (B7h, GL50, BRP-1, B7-H2, LICOS), ICOS-binding variants of ICOS-L, or ICOS-binding fragments of ICOS-L, preferably soluble ICOS-L or a soluble fragment or variant of ICOS-L. Preferably the ICOS-L comprises the extracellular region comprising residues 1 to 258 of human ICOS-L (Ling V et al., J. Immunol. 2000, 164:1653-1657). This sequence may be modified to optimize binding affinity to ICOS.

The term "effector molecule" as used herein includes, for example, antineoplastic agents, drugs, toxins, biologically active proteins, enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

In preferred embodiments the effector molecule is responsible for causing the in vivo depletion of the ICOS-positive cells to which it is bound. In one embodiment the effector molecule is capable of recruiting and activating complement or mediating antibody-dependent cellular cytotoxicity (ADCC) in vivo, or mediating phagocytosis by binding Fc receptors in vivo. Such components may include immunoglobulin Fc region subtypes known to exhibit these characteristics such as human IgG1 and IgG3, murine IgG2a or rat IgG2b. These immunoglobulin subtypes may be further modified to enhance these effector functions in vivo.

In another example the effector molecules may be cytotoxins or cytotoxic agents including any agent that is detrimental to (e.g. kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

The ICOS-binding agent may also deplete ICOS-positive cells by inducing apoptosis of that cell upon binding. An ICOS-binding agent may be optimized to deplete ICOS-positive effector T cells, for example in combination with other pharmacological agents, to induce apoptosis in these cells (Yu X Z et al., J. Immunol. 2003, 170:3002-3006).

Techniques for conjugating such effector molecules to proteins are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). In one example, where the ICOS-binding agent is an antibody, the antibody or fragment thereof may be fused via a covalent bond (e.g. a peptide bond), at optionally the N-terminus or the C-terminus, to an amino acid sequence of another protein (or portion thereof; preferably at least a 10, 20 or 50 amino acid portion of the protein). Preferably the antibody, or fragment thereof, is linked to the other protein at the N-terminus of the constant domain of the antibody. Recombinant DNA procedures may be used to create such fusions, for example as described in WO 86/01533 and EP 0392745.

In further embodiments the effector molecule(s) may increase the half-life of the ICOS-binding agent in vivo, and/or enhance the delivery of the ICOS-binding agent, in particular of an antibody, across an epithelial barrier to the immune system and/or reduce the immunogenicity of the ICOS-binding agent.

In a preferred embodiment wherein the ICOS-binding component is an antibody, the antibodies are preferably attached to poly(ethyleneglycol) (PEG) moieties. The antibody may be an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods. See for example U.S. Pat. No. 5,219,996 and U.S. Pat. No. 5,677,425. Multiple sites can be used to attach two or more PEG molecules. Preferably PEG molecules are covalently linked through a thiol group of at least one cysteine residue located in the antibody fragment. Where a thiol group is used as the point of attachment appropriately activated effector molecules, for example thiol selective derivatives such as maleimides and cysteine derivatives may be used.

Preferably, the antibody is a modified Fab' fragment which is PEGylated, i.e. has PEG (poly(ethyleneglycol)) covalently attached thereto, e.g. according to the method disclosed in EP 0948544 (see also "Poly(ethyleneglycol) Chemistry, Biotechnical and Biomedical Applications", 1992, J. Milton Harris (ed), Plenum Press, New York, "Poly(ethylene-glycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545). Preferably PEG is attached to a cysteine in the hinge region. In one example, a PEG modified Fab' fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab' fragment may therefore be approximately 40,000 Da.

In one example the ICOS binding agent of the present invention also blocks the binding of ICOS-L to ICOS. Ligand blocking may be determined by standard flow cytometry or surface plasmon resonance methods.

Preferably ICOS-binding agent, protein or peptide is selected and/or modified to prevent stimulation of ICOS and hence T cell costimulation. Costimulation is preferably detectable as enhanced TCR-mediated T cell activation. Costimulation may be measured in vitro by standard techniques detecting the induction of enhanced cell proliferation or cytokine production, for example IL-2, IFN-γ, TNF-α, IL-4, IL-5 and IL-10, or cell survival. Costimulation may be detected in vivo by increased immune cell number, particularly T cells, and worsening of disease symptoms in animal models of inflammatory, autoimmune, and allergic diseases, transplantation and cancer.

Depending on the effector molecule(s) selected the ICOS-binding agent for use in the present invention may be selected and/or modified to remain on the cell surface or to be capable of rapid internalisation from the cell surface in vivo. Where at least one of the effector molecule(s) is a cytotoxic agent, it is preferable that the ICOS-binding agent is rapidly internalised from the cell surface into the ICOS positive cell. Internalisation of the ICOS-binding agent into the ICOS-positive cell in vivo may be measured by standard flow cytometry or fluorescence microscopy.

As discussed herein below, the present invention also refers to favourable uses of the ICOS-binding agents of the present invention in the treatment of diseases.

A second aspect of the present invention therefore refers to a pharmaceutical composition comprising an ICOS-binding agent which in vivo depletes ICOS-positive cells and a pharmaceutically acceptable diluent, excipient and/or carrier. The ICOS-binding agent may be selected from any embodiment of the invention. Preferably, the pharmaceutical composition comprises a pharmaceutically effective amount of at least one or more ICOS-binding agents, in particular at least one antibody or antibody fragment which binds to ICOS expressed on the surface of cells, preferably activated T cells.

A third aspect of the present invention refers to the use of an ICOS-binding agent which depletes ICOS-positive cells in vivo for the manufacture of a medicament for the treatment or prophylaxis of a condition mediated directly or indirectly by cells expressing ICOS on their surface. The ICOS-positive cells are preferably activated T cells. Preferably, the medicament is for the prophylaxis or the treatment of a condition such as e.g. a T cell mediated overreaction to a pathogen, an autoimmune disease, inflammatory disease, an allergic reaction, a transplanted organ rejection, a graft-versus-host disease, or cancer.

Preferably, the medicament is for the prophylaxis or the treatment of autoimmune diseases, such as rheumatoid arthritis, ankylosing spondylitis, Sjögren's syndrome, inflammatory bowel diseases (colitis ulcerosa, Crohn's disease), multiple sclerosis, sarcoidosis, psoriasis, systemic lupus erythematosus, vasculitis, and others. The prophylaxis or treatment provided by the present invention also refers to organ rejection or the graft versus host disease, allergic diseases such as allergic asthma, food and bee venom allergy. It also refers to the elimination of cancer cells which express the ICOS molecule on the cell surface from the body of a patient.

For such use the ICOS-binding agents will preferably be administered in the form of a pharmaceutical composition.

The term "treatment" as used herein preferably includes either therapeutic or prophylactic therapy. When a reference is made herein to a method of treating or preventing a disease or condition using a particular ICOS-binding agent it is to be understood that such a reference is intended to include the use of that ICOS-binding agent for the manufacture of a medicament for the treatment and/or prophylaxis of disease. The ICOS-binding agents for use in the invention may be administered in combination, e.g. simultaneously, sequentially or separately, with one or more other therapeutically active compounds, which may be for example other immunosuppressive agents or anti-cancer therapies.

A fourth aspect of the present invention refers to a method of reducing a population of T cells that express ICOS in a human host, comprising administering an effective amount of an ICOS-binding agent according to any embodiment of the ICOS-binding agent of the present invention. Preferably, the effective amount of the ICOS-binding agent is sufficient for a measurable reduction of the titer of activated T cells in a blood or tissue sample obtained from a patient suffering from one of the immunological diseases mentioned herein.

A fifth aspect of the present invention also refers to a method of treating a patient suffering from a condition mediated directly or indirectly by activated T cells, the method comprising administering to the patient an effective amount of an ICOS-binding agent which therapeutically effectively depletes activated T cells.

As mentioned herein, a sufficient or effective amount of the ICOS-binding agent is preferably a therapeutically effective amount, in particular of a unit dose of administration of a medicament.

A patient as mentioned herein may suffer without limitation from a condition which is selected from the group consisting of allergic asthma, hay fever, bee venom allergy, food allergy, multiple sclerosis, sarcoidosis, rheumatoid arthritis, ankylosing sponylitis, Sjögren's syndrome, systemic lupus erythematosus, inflammatory bowel diseases (colitis ulcerosa, Crohn's disease), psoriasis, vasculitis, T cell lymphoma expressing ICOS, rejection of a transplanted organ or tissue, and graft-versus-host disease. ICOS depletion in vivo will be therapeutically effective in all diseases, in which ICOS$^+$ T cells represent the major population of effector cells, i.e. the T cells that drive the disease process.

The effective dose of the ICOS-binding agent for any particular patient will depend upon a variety of factors including the kind and the severity of the disease, the dosage form, the age, body weight and sex of the patient, the duration of the treatment and like factors well known in the medical arts. Preferably, the unit dose is therapeutically effective for the treatment of an adult, a child, a small child, or a new born.

The total daily dose of the ICOS-binding agent can be in amounts, for example, from about 0.01 to about 50 mg/kg body weight or more preferably from about 0.1 to about 25 mg/kg body weight. Single dose compositions may contain such amounts or submultiples thereof to make up the daily dose. In general, treatment may comprise administration from about 10 mg to about 1000 mg of an ICOS-binding agent per day in single or multiple doses. A combination of more than one ICOS-binding agent may be used for the manufacture of a medicament.

For the production of the medicament an ICOS-binding agent is preferably formulated with one or more pharmaceutically acceptable additives or auxiliary substances, such as physiological buffer solution, e.g. sodium chloride solution, demineralized water, stabilizers, such as protease or nuclease inhibitors, preferably aprotinin, ϵ-aminocaproic acid or pepstatin A or sequestering agents such as EDTA, gel formulations, such as white vaseline, low-viscosity paraffin and/or yellow wax, etc. depending on the kind of administration.

Suitable further additives are, for example, detergents, such as, for example, Triton X-100 or sodium deoxycholate, but also polyols, such as, for example, polyethylene glycol or glycerol, sugars, such as, for example, sucrose or glucose, zwitterionic compounds, such as, for example, amino acids such as glycine or in particular taurine or betaine and/or a protein, such as, for example, bovine or human serum albumin. Detergents, polyols and/or zwitterionic compounds are preferred.

The physiological buffer solution preferably has a pH of approx. 6.0-8.0, especially a pH of approx. 6.8-7.8, in particular a pH of approx. 7.4, and/or an osmolarity of approx. 200-400 milliosmol/liter, preferably of approx. 290-310 milliosmol/liter. The pH of the pharmaceutical composition is in general adjusted using a suitable organic or inorganic buffer.

The pharmaceutical composition or medicament comprising an ICOS-binding agent can be administered in a conventional manner, e.g. by means of oral dosage forms, e.g. tablets or capsules, by means of the mucous membranes, e.g. of the nose or the oral cavity, by means of inhalation, injections, infusions or gels. It is further possible to administer the pharmaceutical composition topically and locally, in the form of liposome complexes. Furthermore, the treatment can be carried out by means of a transdermal therapeutic system (TTS), which makes possible a temporally controlled release of the pharmaceutical compositions. TTS are known for example, from EP 0 944 398 A1, EP 0 916 336 A1, EP 0 889 723 A1 or EP 0 852 493 A1.

The pharmaceutical composition can be manufactured for oral, nasal, rectal, parenteral, intratracheal, topic or vaginal administration. Parenteral administration includes subcutaneous, intracutaneous, intramuscular, intravenous or intraperitoneal administration, in particular using suitably prepared injection or infusion solutions.

A sixth aspect of the present invention refers to a method of screening an ICOS-binding agent, wherein the method comprises the steps of: (a) providing ICOS-bearing cells, (b) providing a test compound, and (c) measuring or detecting the influence of the test compound on the depletion of the ICOS-bearing cells.

In a preferred embodiment, the test compound is provided in the form of a chemical compound library. Preferably, the term "chemical compound library" refers to a plurality of chemical compounds that have been assembled from any of multiple sources, including chemically synthesized molecules and natural products, or that have been generated by combinatorial chemistry techniques.

The test compound may in principle be any chemical compound, such as a naturally occurring compound, or a chemically synthesized compound that is identical or similar to a naturally occurring compound, or any chemically synthesized compound that does not occur in nature.

A naturally occurring compound may be a compound that can be detected in or isolated from a multicellular or single cell organism, in particular a compound that can be detected in or isolated from an animal, a plant, a fungus, a yeast, bacterium, or any other cell-containing organism or in a virus. A chemically synthesized compound that does not occur in nature may be synthesized by combinatorial chemistry.

Preferably, a test compound comprises a lead structure derived from a naturally occurring compound, preferably a lead structure of a peptide or protein which binds to ICOS. Preferably, the test compound is an antibody or fragment thereof which is derived from an immunization of an animal using a soluble ICOS-derivative, e.g. like the fusion protein in Example 1, below, or a human ICOS-derivative. The test compound may also be an recombinant derivative of an anti-ICOS antibody or fragment thereof.

The test compound may be any anti-ICOS antibody, preferably an antibody reacting with ICOS located on the surface of an activated T cell. Preferably, the test compound comprises a monoclonal anti-ICOS antibody or a fragment thereof, in particular a recombinantly produced derivative or fragment of a monoclonal anti-ICOS antibody, in particular a humanized monoclonal antibody or fragment thereof or an antibody fragment comprising at least one, preferably all three complementarity determining regions (CDRs) of an anti-ICOS antibody.

The ICOS-bearing cell is preferably an activated T cell, preferably a human T cell, or a recombinant animal or human cell bearing a T cell receptor, preferably a human T cell receptor. Activated T cells may be isolated from a patient suffering preferably from an overreaction to a pathogen, an autoimmune disease, inflammation, an allergic reaction, a transplanted organ rejection, a graft-versus-host disease, or a lymphoma, preferably as mentioned within any embodiment of the present invention.

In alternative, the ICOS-bearing activated T cells may be derived from an experimental animal, in particular from a T cell receptor transgenic animal. The ICOS-bearing activated T cells may be obtained by stimulation of T cells wherein an antigen specifically recognized by a T cell receptor is used or by using a polyclonal T cell activator like e.g. Staphylococcal Enterotoxin B (SEB). Transgenic T cells are preferably stimulated with the antigen recognized by the transgenic T cell receptor.

The ICOS-bearing activated T cells may be generated by in vivo stimulation, in particular by immunizing or rechallenging an animal comprising transgenic T cells, and/or by in vitro stimulation or restimulation, e.g. such as in the generation of the ICOS-bearing T cells in the Examples 2 to 5, below. The influence of the test compound on the ICOS-bearing cells may be screened using in vitro assays and/or using an in vivo animal model.

In the following, several especially preferred embodiments pertaining to all aspects of the present invention, and preferably pertaining to the method of screening an ICOS-binding agent according to the sixth aspect of the invention, are described.

Generation of ICOS-expressing cells. ICOS expressing cells can be generated by activating primary human T cells, e.g. with antigen or with polyclonal stimulators like phytohemagglutinin or phorbol myristate acetate in combination with ionomycin. Alternatively, ICOS-expressing cells can be generated by transfecting appropriate cell lines with a eukaryotic expression vector containing the cDNA for an extracellular portion of ICOS. Activated T cells, T cell clones or transfectants can be monitored for optimal ICOS expression by staining with an ICOS-specific mAb or by staining with soluble ICOS-L and analyzed using flow cytometry.

Generation of recombinant ICOS polypeptide. The recombinant polypeptide containing sequences of the extracellular portion of human ICOS can be expressed in E. coli or any eukaryotic expression system (e.g. yeast, animal or human cell lines) with the use of appropriate expression vectors by standard techniques. To facilitate purification, a suitable tag can be attached to the ICOS polypeptide, e.g. a His-tag or a constant region of an antibody. In the case that the polypeptide can be expressed in E. coli only in a denatured form in inclusion bodies, the polypeptide can be fully denatured, subsequently renatured in a suitable buffer, and then purified to homogeneity using standard chromatography techniques.

Generation of an ICOS-binding agent by expressing the extracellular portion of ICOS-L. The extracellular portion of ICOS-L binds to ICOS with a high specificity and can be used as an ICOS-binding agent. To improve the affinity of ICOS-L to ICOS, the cDNA encoding the extracellular portion of ICOS-L involved in the binding to ICOS can be mutagenised by standard techniques. In the natural form or in the optimized form, the ICOS-binding region of ICOS-L can be used as a component of a depleting ICOS-binding agent generated by recombinant techniques.

Generation of an ICOS-binding agent by immunization of animals. An ICOS-binding agent can be generated by immunizing an animal (e.g. mouse, rat, hamster, rabbit) with ICOS-expressing cells, or with a recombinant protein containing the entire or partial extracellular portion of human ICOS. B cell blasts from the immunized animal (e.g. from the spleen, lymph node, bone marrow or peripheral blood) can be fused to a permanent cell line (e.g. myeloma or an oncogene-driven permanent line) to generate a hybridoma line secreting ICOS-specific mAbs. Alternatively, B cell blasts from the immunized animal are selected for ICOS-binding and used to clone the cDNA coding for the ICOS-binding region of the B cell receptor. This cloned IgG-V-region can be used for the engineering of a recombinant ICOS-binding agent. Alternatively, an ICOS-binding agent can also be generated using single lymphocyte antibody methods by cloning and expressing immunoglobulin variable region cDNAs generated from single lymphocytes selected for the production of specific antibodies by for example the methods described by Babcook, J. et al, 1996, Proc. Natl. Acad. Sci. USA 93(15):7843-7848 and in WO92/02551.

Generation of an ICOS-binding agent by screening of a synthetic repertoire. Instead of immunizing animals, an ICOS-binding agent can be isolated from a synthetic repertoire, e.g. an antibody-display library. A respective (e.g. phage-) display-library is screened for an ICOS-binding agent by ELISA or any suitable affinity-based technique (e.g. panning). To ensure high affinity binding of the ICOS-polypeptide, the coding cDNA sequence of the binding agent is isolated and subjected to a random mutagenesis procedure (e.g. error-prone PCR, DNA shuffling, site-directed PCR). The mutagenised cDNA coding for the binding agent is re-expressed and re-screened for optimal binding of the extracellular ICOS polypeptide. This final cDNA is then used as a component to construct a biologically useful ICOS-binding agent (e.g. antibody, partial antibody, etc.).

Screening of the ICOS-binding agent for an affinity which is required for in vivo depletion without adverse effects. Whatever the type and source of the ICOS-binding agent (ICOS-L construct, mAb obtained from an immunized animal or a recombinant binding agent derived from B cell blasts or a synthetic repertoire), the ICOS binding agent is screened for binding to ICOS with an affinity optimal for in vivo depletion. To this end, a recombinant form of the extracellular ICOS polypeptide or cells expressing ICOS are used as a target for a binding assay. One of the binding partners (ICOS polypeptide or the ICOS-bind agent) is immobilized and the binding characteristics of the other (labelled) component are observed in a suitable assay (e.g. Biacore). ICOS binding agents with an appropriate binding constant are selected.

Screening of the ICOS-binding agent for specificity. Where desired the binding agent may be screened for specificity to ICOS using for example, flow cytometry and/or immunohistochemistry.

Engineering of the ICOS-binding agent to minimize immunogenicity in the human. If the ICOS-binding agent is not derived from a human antibody, it can be "humanized" to prevent the development of neutralizing antibodies in the treated patient. To this end, the regions responsible for the binding of the extracellular ICOS polypeptide are "grafted" onto a human polypeptide framework (e.g. IgG constant region) using standard molecular biology techniques, so that the recombinant ICOS-binding agent largely contains non-immunogenic human protein sequences.

Engineering of the ICOS-binding agent for optimal binding of complement in vivo. Binding of complement can be utilized to deplete ICOS-positive cells (ICOS-positive cells) from the circulation. To this end, the ICOS binding agent is engineered to contain regions ensuring optimal binding of complement. In vivo, the binding of complement to the ICOS-binding agent will trigger the death of the ICOS-bearing cell. The ICOS-binding agent can be tested in vitro for this effect using an assay-system containing live ICOS-bearing cells, the ICOS-binding agent and human complement. The effectiveness of complement-binding can be measured e.g. by the decrease of soluble complement in the liquid phase over time or by measuring cell death of the ICOS-bearing cells using standard methods (e.g. $^{51}$chrome-release, release of an intracellular dye, or counting of live cells).

Engineering of the ICOS-binding agent for optimal induction of phagocytosis of ICOS-positive cells in vivo. Depletion of ICOS-positive cells in vivo can be achieved through phagocytosis of ICOS-positive cells by phagocytic cells (e.g. macrophages, Kupffer cells of the liver, gut and lung macrophages, spleen macrophages) mediated by the ICOS-binding agent. This can be e.g. an Fc-receptor-mediated phagocytosis or a phagocytosis induced using an ICOS-binding agent which is bivalent in that it recognizes ICOS and also a suitable target (e.g. Fc receptor) on phagocytic cells. An ICOS-binding agent can be selected for optimal phagocytosis-inducing action by culturing ICOS-positive cells together with phagocytic cells in the presence of variable amounts of the ICOS-binding agent. The degree of phagocytosis is determined by standard assays, e.g. by labelling the ICOS-positive cells and the phagocytic cells with differently coloured dyes followed by an assay determining the degree of phagocytosis by standard microscopic techniques.

Screening of the ICOS-binding agent for minimal activation of primary ICOS-bearing cells. To generate an ICOS-binding agent capable of removing ICOS-positive cells from the circulation of a patient through activation of complement or through phagocytosis, it is desirable to use an ICOS-binding agent with minimal or absent co stimulatory activity, which could lead to untoward cell activation or expansion in vivo. The screening of the ICOS-binding agent for minimal T cell co stimulatory activity is performed in vitro using a standard co-stimulation assays, for example using suboptimal amounts of mAb OKT3 bound to a solid phase in combination with titrated amounts of the ICOS-binding agent also bound to a solid phase. An ICOS-binding agent lacking co-stimulatory activity would not increase the degree of cell proliferation or cytokine synthesis observed with the mAb OKT3 alone.

Engineering of the ICOS-binding agent for induction of ICOS-binding agent-dependent cytotoxicity in vivo. Antibody-dependent cytotoxicity is a well characterized phenomenon and can be observed, e.g. when mAb bind with their antigen-binding region to a target cell and with their Fc-region to Fc-receptors on cytotoxic cells (e.g. CD16 on NK cells). The induced crosslinking of the Fc-receptor (e.g. CD16) activates the cytotoxic capacity of the cytotoxic cells which lyse the target cell. Other cells, e.g. macrophages, also exhibit antibody-dependent cytotoxicity. An ICOS-binding agent can be optimized for mediating this type of cytotoxicity by choosing an optimal Fc-region as a part of the protein construct. Testing of such an agent in vitro for induction of cytotoxicity is a standard procedure. ICOS-bearing target cells are cultured with the ICOS-binding agent in the presence of NK cells or other cytotoxic cells and the degree of target cell lysis (release of label) induced by the ICOS-binding agent is measured over time.

Engineering of the ICOS-binding agent for induction of apoptosis in ICOS-positive cells in vivo. Since ICOS is expressed on effector T cells, which are more prone to apoptosis compared to naive or memory T cells, an alternative way to deplete ICOS-positive T cells in vivo can be achieved through induction of apoptosis in these cells. The apoptosis of the ICOS-positive target cell is measured by standard assays (e.g. tunnel assay).

Engineering of an ICOS-binding agent for optimal internalization in vivo. An optimal in vivo depleting effect of an ICOS-binding agent covalently bound to a cytotoxin in many cases requires rapid internalization of the ICOS-binding agent. Therefore, an ICOS-binding agent is engineered which recognizes an epitope on ICOS which induces a rapid internalization of ICOS. Alternatively, the ICOS-binding agent bivalently recognizes an additional cell surface molecule on the ICOS-positive cells and through this double-specificity induces a rapid internalization of ICOS. The internalization of ICOS can be measured in vitro by standard assays, e.g. by fluorescently labelling the ICOS-binding agent followed by standard microscopy analysis (internalization of the fluorescent signal).

Engineering and testing of an ICOS-binding agent after injection into a body compartment (e.g. subcutaneously, intraperitoneally, intratracheally, intravenously or intramuscularly) for optimal depletion of ICOS-positive cells in vivo. This approach can be used as a final functional screen for any of the depletion properties of the ICOS-binding agent outlined above (e.g. depletion through phagocytosis, antibody-dependent cytotoxicity, apoptosis, internalization of a cytotoxin, complement binding) or as the sole screening approach for the selection of an optimally depleting ICOS-binding agent. If the ICOS binding agent recognizes an ICOS-epitope shared by human and rat or human and mouse ICOS (Buonfiglio et al., Eur. J. Immunol. 1999, 29:2863-2874), the screening-test can be performed directly in an animal system (e.g. rat or mouse). This includes testing of phagocytosis-mediated depletion, since human mAb are capable of binding to animal Fc-receptors on phagocytic cells and to induce phagocytosis (Isaacs J D, Rheumatology 2001, 40:724-738). A suitable animal system can be the allergic lung inflammation model (see Example 5, below). Alternative standard disease models, e.g. inflammatory bowel disease models, transplantation models or autoimmune models are equally appropriate. If the ICOS-binding agent recognizes an epitope shared by the human and a primate animal only, the testing of the depletion capacity of the ICOS-binding agent can be tested in the primate animal (e.g. transplantation model, inflammation model). The depletion of ICOS-positive cells in vivo can also be achieved by engineering an ICOS-binding agent in which the ICOS-binding region is grafted onto the immunoglobulin framework (constant region which mediates the biological effects) of an antibody with established depleting capacity in the human, e.g. the cM-T412 mAb directed to the CD4 cell surface molecule on T cells (Isaacs J D, Rheumatology 2001, 40:724-738). An alternative screening system for an ICOS-binding agent specific for human ICOS, but not recognizing mouse or rat ICOS, can be a "humanized" animal model, e.g. a "humanized" SCID mouse. ICOS-positive human cells can be transferred into such an animal and are not rejected, since these animals lack T and B cells. After transfer of the human ICOS-positive cells, these animals are treated with the ICOS-binding agent of choice as described above. In all in vivo models, the capacity of the ICOS-binding agent to deplete ICOS-positive cells can be assessed in a standard fashion. Among others, following parameters can be determined 1) The levels of ICOS-positive cells in the circulation or in body organs by flow cytometry or histology; 2) if the transferred ICOS-positive cells carry a marker (e.g. allo-marker, transgenic receptor, fluorescent label), the percentage of marker-positive cells; 2) the degree of inflammatory infiltrate in the target organ; 3) parameters of systemic inflammation (e.g. C-reactive to protein); 4) organ function (e.g. blood sugar levels in an autoimmune model of diabetes); 5) weight; 6) clinical disease score.

A seventh aspect of the present invention refers to a method for producing a medicament for the treatment of a condition mediated directly or indirectly by T cells, wherein the method comprises the steps of (a) carrying out the method of the invention of screening an ICOS-binding agent, (b) isolating a measured or detected test compound suitable for the treatment of a condition mediated directly or indirectly by T cells, and (c) formulating the measured or detected test compound with one or more pharmaceutically acceptable carriers.

In a preferred embodiment, the condition that shall be treated is a T cell mediated allergic or autoimmune disease, inflammatory disease or a cancer. Preferably, said condition is an overreaction to a pathogen, an autoimmune disease, an allergic reaction, a transplant organ rejection, a graft-versus-host disease, or a cancer. Preferably, said condition may be selected from the group consisting of allergic asthma, hay fever, bee venom allergy, food allergy, multiple sclerosis, sarcoidosis, rheumatoid arthritis, ankylosing sponylitis, Sjögren's syndrome, systemic lupus erythematosus, inflammatory bowel diseases (colitis ulcerosa, Crohn's disease), psoriasis, T cell lymphoma expressing ICOS, rejection of a transplanted organ or tissue, and graft-versus-host disease.

An eighth aspect of the present invention refers to an ICOS-binding agent which can be identified using the method of the invention of screening an ICOS-binding agent.

BRIEF DESCRIPTION OF THE DRAWINGS

In the following, the invention is described with reference to FIGS. 1 to 5 without any limitation in Examples 1 to 6. The Figures show:

FIG. 1: Establishment of an in vivo model for the testing of mAb directed to ICOS for their depletion capacity.

EXAMPLES

Example 1

Generation of mAb Against Murine ICOS

LEWIS rat were immunized with soluble chimeric murine ICOS-rabbit-Ig fusion protein as described (Mages H W et al., Eur. J. Immunol. 2000, 30:1040-1047), the spleen cells fused with myeloma P3X63Ag8.653 (American Type Culture Collection) by standard techniques and the resulting hybridomas were screened by flow cytometry using L-cells transfected with murine ICOS (Mages H W et al., Eur. J. Immunol. 2000, 30:1040-1047). Using this approach 12 different mAb directed against murine ICOS were obtained.

Example 2

Figure 1:
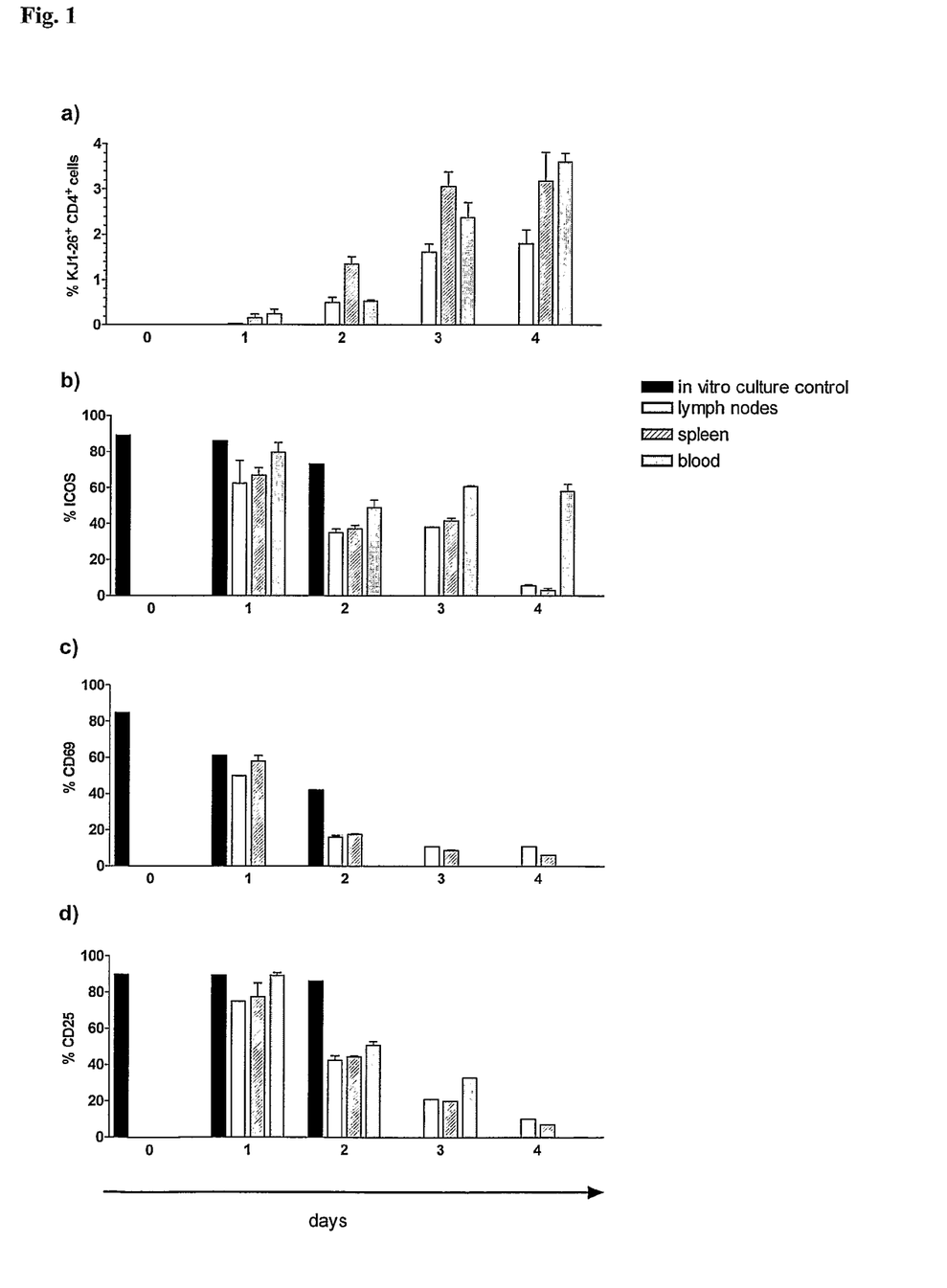

Establishment of an In Vivo Model for Testing of ICOS-Specific mAb for Depletion Capacity Spleen cells from DO11.10 mice, which contain T cells with a transgenic receptor specific for ovalbumine (OVA) were stimulated with $OVA_{323-339}$ peptide for 3 days in vitro. At the end of this culture 90% of the transgenic T cells expressed ICOS. The transgenic T cells were then transferred by the i.v. route into syngeneic BALB/c mice ($10 \times 10^6$ T cells/mouse). On days 1, 2, 3, and 4 after transfer the transgenic T cells (which can be traced using mAb KJ1-26 directed to the transgenic T cell receptor) were analyzed in the lymph nodes (LN), spleen and blood for the expression of the activation surface molecules ICOS, CD69 and CD25. The experiment demonstrated that the activated, ICOS-positive T cells continue to expand in vivo and represent up to 4% of all lymphocytes in the examined compartments on day 4 (FIG. 1a). The experiment also showed that the transferred transgenic T cells continue to express ICOS over days in vivo (FIG. 1b), to a lower extent also the activation molecules CD69 and CD25, which are downregulated in a more rapid fashion (FIGS. 1c and d).

Example 3

Figure 2:
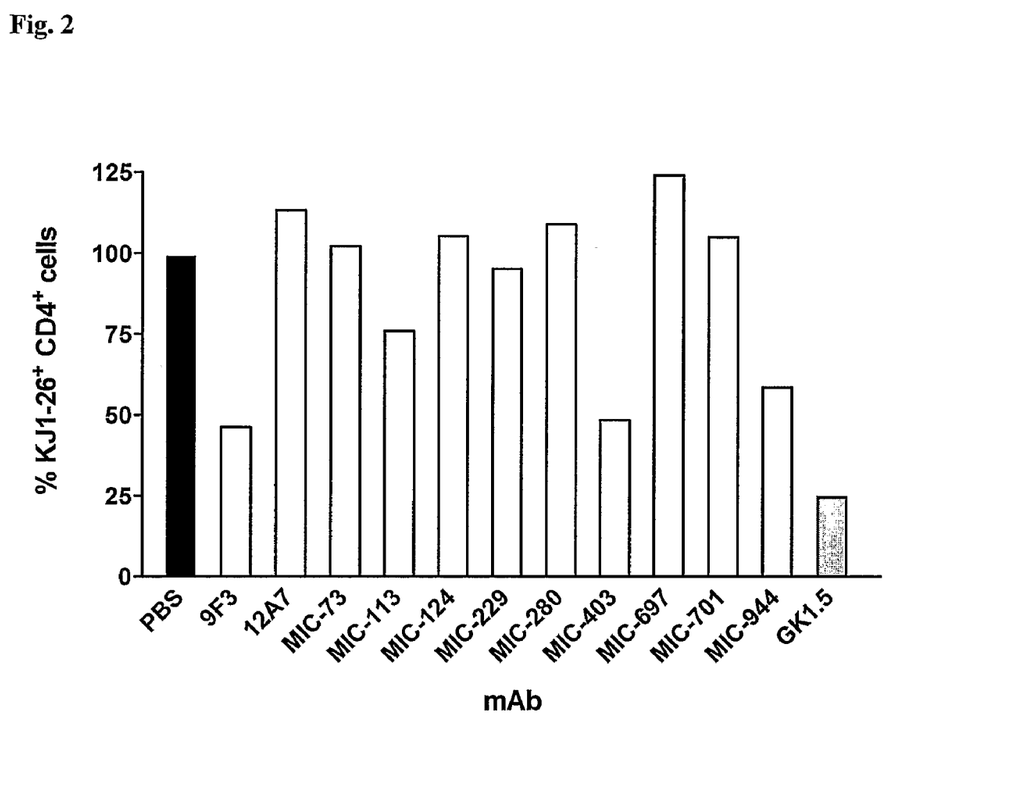
FIG. 2: Testing of mAb directed to murine ICOS for depletion in vivo after adoptive transfer of transgenic ICOS-positive OVA-specific T cells without local application of OVA.

Testing of mAb Directed to Murine ICOS for Depletion In Vivo after Adoptive Transfer of Transgenic ICOS-Positive OVA-Specific T Cells without Local Application of OVA The basic setup of the experiment was as described in Example 2. After 2 days of in vitro culture with OVA peptide, $5 \times 10^6$ DO11.10OVA-TCR transgenic KJ1.26$^+$ T cells (50% of them ICOS-positive) were transferred i.v. into BALB/c mice. Various ICOS-specific mAb were administered i.p. at a dose of 500 µg in 300 µl PBS immediately after transfer. The negative control was treatment with PBS, treatment with mAb GK1.5 (an anti-CD4 mAb with known depletion capability) served as a positive control. On day 6 the peripheral LN were removed and analyzed for the percentage of transgenic KJ1.26$^+$ T cells by flow cytometry (sham-treatment with PBS=100%). This experiment determined that in the absence of OVA (the antigen recognized by the transgenic T cells) some mAb (MIC-944, 9F3 and MIC-403) effectively depleted ICOS-positive T cells in vivo, whereas other ICOS-specific mAb were without effect or, in the case of 12A7 and MIC-697 caused an increase in ICOS-positive T cells (FIG. 2).

Example 4

Figure 3:
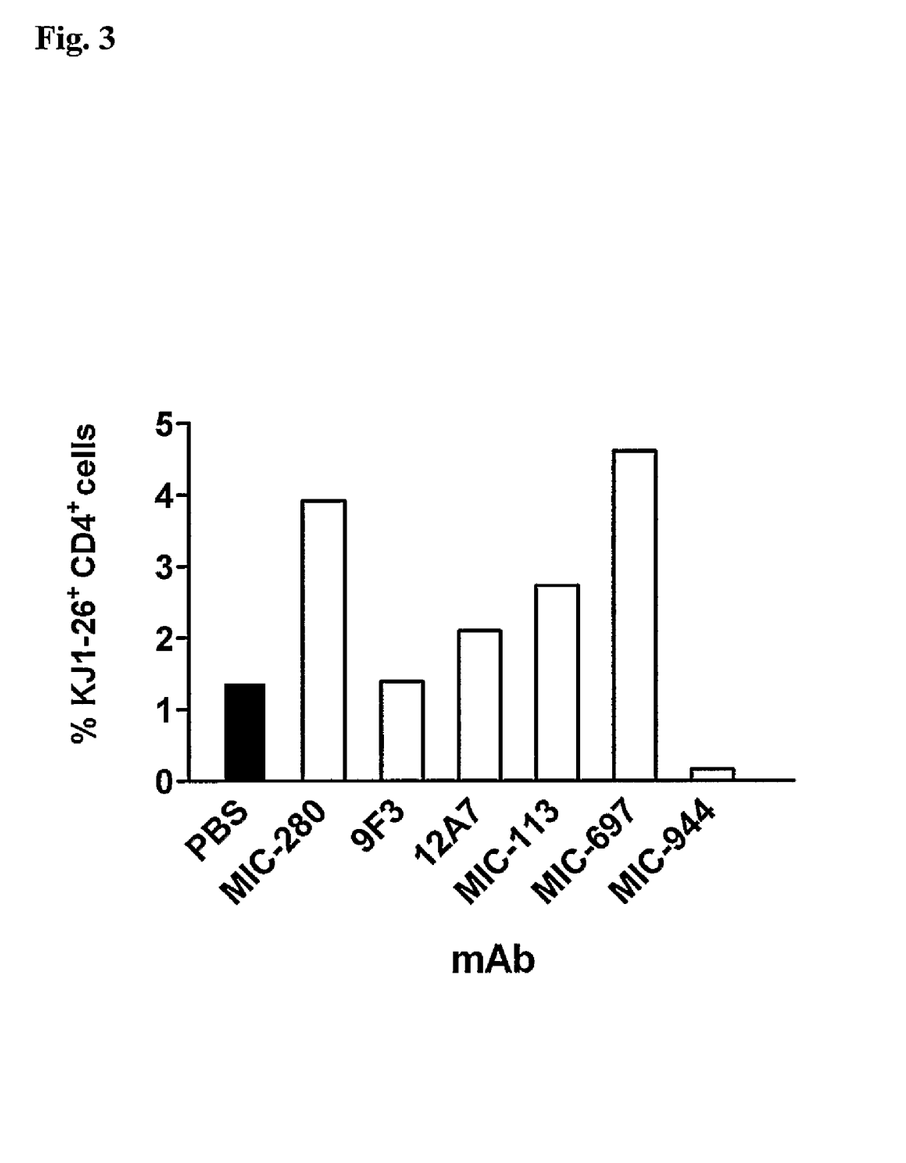
FIG. 3: Testing of mAb directed to murine ICOS for depletion in vivo after adoptive transfer of transgenic ICOS-positive OVA-specific T cells and local application of OVA in complete Freund's adjuvant.

Testing of mAb Directed to Murine ICOS for Depletion In Vivo after Adoptive Transfer of Transgenic ICOS-Positive OVA-Specific T Cells and Local Application of OVA in Complete Freund's Adjuvant It was desirable to test whether antibodies directed to ICOS would deplete ICOS-positive cells in vivo also in the presence of the antigen OVA without any undesirable co-stimulatory effects. DO11.10 spleen cells were stimulated with OVA-peptide for 48 h in vitro. From this culture $10 \times 10^6$ OVA-specific transgenic CD4$^+$ T cells (80% of them ICOS-positive at the end of culture) were transferred to BALB/c recipients by i.v. injection. Two days before transfer, the recipient mice had been immunized subcutaneously at 4 separate regions on the back with 200 µg OVA in complete Freund's adjuvant to provide the OVA-antigen to the immune system. Mice were then treated with the indicated mAb (200 µg intraperitoneally (i.p.) per injection) on days 0 (day of transfer), 1, and 3. On day 5 the draining inguinal LN were removed and analyzed by flow cytometry for the presence of KJ1-26$^+$ transgenic T cells. This experiment demonstrated that treatment with mAb MIC-944 strongly reduced the number of OVA-specific T cells in vivo compared to control animals treated with PBS alone in the presence of the nominal antigen OVA (FIG. 3). The application of other ICOS-specific mAb slightly (12A7, MIC-113) or significantly (MIC-697, MIC-280) increased the number of transgenic T cells in vivo. This experiment determined a) that depletion of ICOS-positive T cells in vivo is possible using certain mAb directed to ICOS, b) that other mAb directed to ICOS can have an untoward opposite effect, i.e. expansion of ICOS-positive cells in vivo when the antigen is present, by stimulating ICOS signalling.

Example 5

Figure 4:
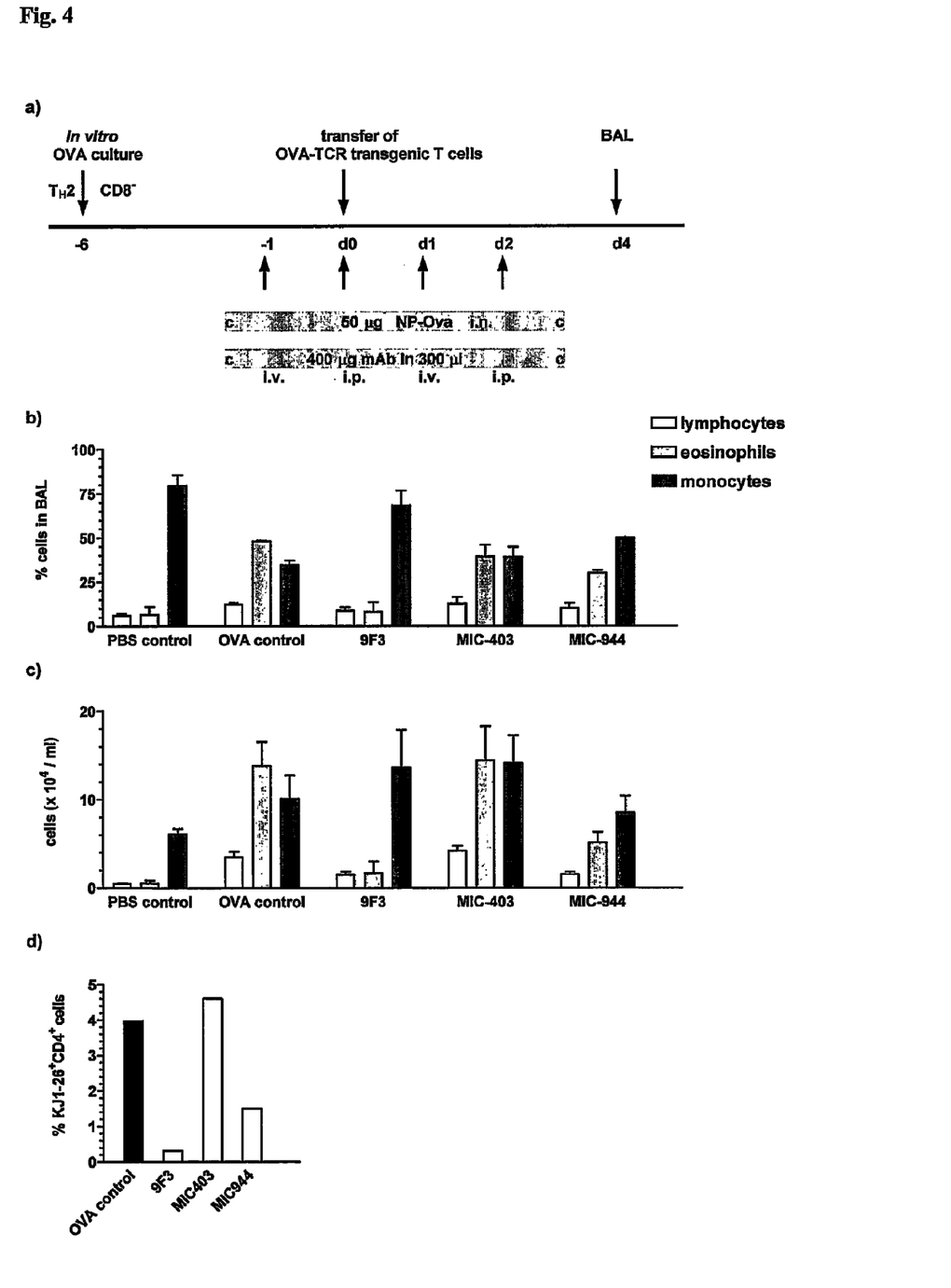
FIG. 4: Experimental setup used to analyze the effect of anti-ICOS antibodies in the airway allergic inflammation model in BALB/c mice.

Prevention of Allergic Lung Inflammation Through Depletion of ICOS-Positive T cells We tested whether mAb's directed to murine ICOS can prevent allergic inflammation in a murine model of allergic asthma. DO11.10 splenic cells were depleted of CD8$^+$ T cells and cultured under Th2-polarizing conditions for 6 days in the presence of OVA peptide$_{323-339}$, with addition of IL-2 on day 5. Under these conditions the transgenic T cells differentiate to produce pro-inflammatory pro-allergic cytokines IL-4, IL-5 and IL-13. After the 6 day culture period the transgenic T cells ($2 \times 10^6$/mouse) were transferred by i.v. injection into syngeneic BALB/c mice. 95% of the transferred cells were transgenic T cells, 90% of which were ICOS-positive. The recipient mice were exposed to the antigen OVA (50 µg) by intranasal (i.n.) application on the day before transfer (d−1), on the day of transfer (d0) and on days 1 and 2 after transfer (FIG. 4a). In this model, the transgenic T cells migrate to the lungs, become activated by the locally applied OVA antigen, release proallergic/proinflammatory mediators and thus induce an allergic inflammation of the lung. The degree of the allergic inflammation can be measured by the appearance of eosinophils and to a lesser degree lymphocytes in the bronchi of the animals. The degree of the lung inflammatory response was assessed by removal of bronchoalveolar lavage (BAL) on day 4 after transfer and analysis of the cells present in the BAL by flow cytometry and microscopic cell differentiation. The recipient animals were treated with 400 µg of ICOS-specific mAbs 9F3 or MIC-403 or MIC-944 on days −1, 0, 1, 2 by alternating i.v. and i.p. injections (FIG. 4a). Negative control animals received PBS i.n. and were sham-treated by PBS ("PBS control"). Positive control animals received OVA i.n., and a sham-treatment with PBS ("OVA-control"). The data in FIG. 4b and c demonstrate that only the application of mAb 9F3 resulted in a complete suppression of the allergic inflammatory reaction in the lung (i.e. a reduction to the levels observed in the "PBS control"). Some suppressive effect was also observed with mAb MIC-944, but no anti-allergic effect was achieved by treatment with mAb MIC-403. Further analysis by flow cytometry revealed that mAb 9F3 effectively reduced the number of transgenic, KJ1-26$^+$ CD4$^+$ T cells in the BAL (FIG. 4d). Reduction of the transgenic T cells was also achieved with mAb MIC-944, but no reduction was observed with mAb MIC-403. These experiments determined that the development of an allergic inflammation of the lung can be effectively prevented by application of anti-ICOS mAb. Further, the experiments demonstrated that careful selection of anti-ICOS mAbs is necessary to demonstrate efficacy in animal models resembling human allergic lung asthma. The methods described here represent an example of how such antibodies may be identified.

Example 6

Expression of ICOS on Cancer Cells

Figure 5:
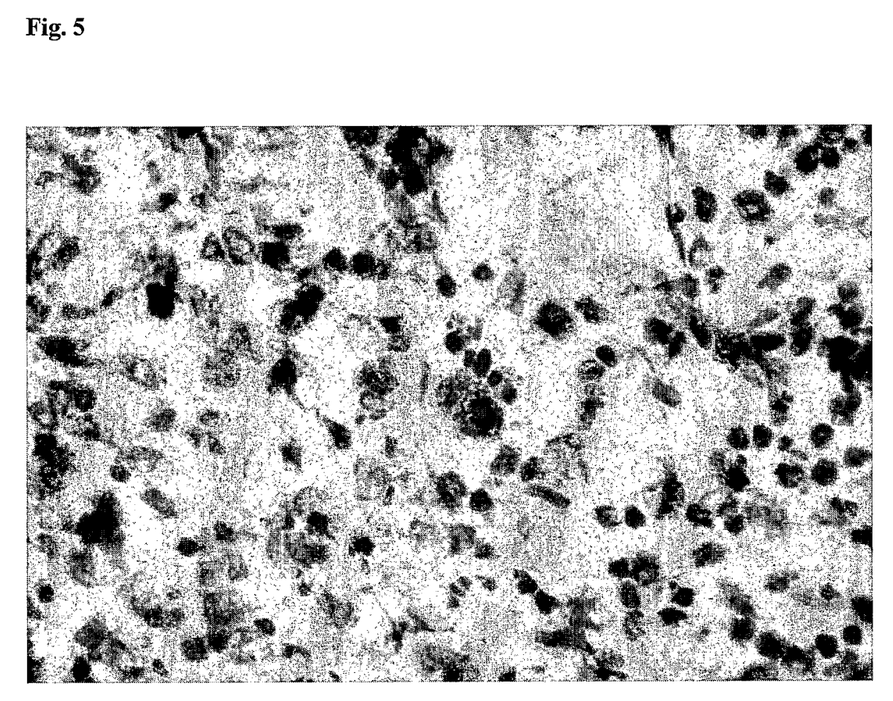
FIG. 5: Staining of human angioimmunoblastic lymphoma with ICOS-specific mAb F44 demonstrating the expression of ICOS by cancer cells.

Tissue sections from a human angioimmunoblastic lymphoma were stained with mAb F44 directed to human ICOS (Hutloff A et al., Nature 1999, 397:263-266) using APAAP, a standard immunohistological technique (FIG. 5). The staining pattern indicates that this lymphoma expresses ICOS on the cell surface, demonstrating that ICOS-specific antibodies could identified for use in the depletion of ICOS-positive cells in cancer patients.

The invention claimed is:

1. An ICOS-binding agent selected from an antibody or antibody fragment, wherein said agent once bound to ICOS expressed on the surface of cells, in particular ICOS-bearing T cells, results in the in vivo depletion of the cells to which it is bound.

2. The ICOS-binding agent according to claim 1 in which the antibody is, or cross-competes with, a monoclonal antibody secreted by the hybridoma cell line MIC-944, deposited at the Deutsche Sammlung von Mikroorganismen and Zellkulturen GmbH (DSMZ) under the accession number DSM ACC 2645, or by the hybridoma cell line 9F3, deposited at the DSMZ under the accession number DSM ACC 2646.

3. The ICOS-binding agent according to claim 1, wherein ICOS is human ICOS.

4. The ICOS-binding agent according to claim 3 which binds to a functionally equivalent epitope to that bound by the antibodies of claim 2.

5. The ICOS-binding agent according to claim 1 which comprises an ICOS-binding agent conjugated to one or more effector molecule(s).

6. The ICOS-binding agent according to claim 5 in which at least one effector molecule is a cytotoxic agent.

7. The ICOS-binding agent according to claim 5 in which the antibody or antibody fragment includes an immunoglobulin Fc region.

8. The ICOS-binding agent according to claim 1 in which the anti-ICOS antibody or fragment thereof is monoclonal, polyclonal, chimeric, humanised, bispecific, multispecific, in particular a recombinant antibody or antibody fragment.

9. The ICOS-binding agent according to claim 8 in which the anti-ICOS antibody fragment is a Fab, Fab', F(ab')2 or scFv, in particular a recombinant antibody fragment.

10. The ICOS-binding agent according to claim 1 in which the binding of the ICOS-binding agent to ICOS prevents the binding of ICOS-L to ICOS.

11. The ICOS-binding agent according to at claim 1 which binds ICOS without stimulating ICOS signalling.

12. The ICOS-binding agent according to claim 1 which is internalised into the cell upon binding to ICOS.

13. The ICOS-binding agent according to claim 1 which is not internalised into the cell upon binding to ICOS.

14. A pharmaceutical composition comprising an ICOS-binding agent according to claim 1 in combination with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,318,905 B2 | |
| APPLICATION NO. | : 11/578215 | |
| DATED | : November 27, 2012 | |
| INVENTOR(S) | : Richard Kroczek | |

It is certified that error appears in the above-identified patent and that said Letters Patent is hereby corrected as shown below:

In the Specification

Column 5, Lines 3-4, replace "are to removed" with --are removed--.

Column 17, Lines 17-18, replace "Fe-region" with --Fc-region--.

Column 18, Line 34, replace "C-reactive to protein" with --C-reactive protein--.

Column 20, Line 29, replace "$10\times10^{60}VA$" with --$10\times10^{6} OVA$--.

In the Claims

Column 22, Claim 2, Lines 13-14, replace "and Zellkulturen" with --und Zellkulturen--.

Signed and Sealed this
Twenty-fifth Day of June, 2013

Teresa Stanek Rea
*Acting Director of the United States Patent and Trademark Office*